(12) United States Patent
de Pablo et al.

(10) Patent No.: US 12,042,519 B2
(45) Date of Patent: Jul. 23, 2024

(54) FREEZE-DRIED FORMULATIONS INCLUDING NANOPARTICLES AND METHODS OF FREEZE-DRYING

(71) Applicant: The University of Chicago, Chicago, IL (US)

(72) Inventors: Juan Jose de Pablo, Chicago, IL (US); Johnny D. Alfaro-Perez, Madison, WI (US); Nader Taheri Qazvini, Chicago, IL (US)

(73) Assignee: The University of Chicago, Chicago, IL (US)

( * ) Notice: Subject to any disclaimer, the term of this patent is extended or adjusted under 35 U.S.C. 154(b) by 257 days.

(21) Appl. No.: 16/630,816

(22) PCT Filed: Jul. 13, 2018

(86) PCT No.: PCT/US2018/042063
§ 371 (c)(1),
(2) Date: Jan. 13, 2020

(87) PCT Pub. No.: WO2019/014576
PCT Pub. Date: Jan. 17, 2019

(65) Prior Publication Data
US 2021/0145901 A1    May 20, 2021

Related U.S. Application Data

(60) Provisional application No. 62/532,502, filed on Jul. 14, 2017.

(51) Int. Cl.
*A61K 35/747* (2015.01)
*A61K 9/16* (2006.01)
*A61K 9/19* (2006.01)

(52) U.S. Cl.
CPC .......... *A61K 35/747* (2013.01); *A61K 9/1611* (2013.01); *A61K 9/1623* (2013.01); *A61K 9/1652* (2013.01); *A61K 9/1694* (2013.01); *A61K 9/19* (2013.01)

(58) Field of Classification Search
CPC .................................................. A61K 35/747
See application file for complete search history.

(56) References Cited

U.S. PATENT DOCUMENTS

| | | | |
|---|---|---|---|
| 5,336,264 A | 8/1994 | Constanz et al. | |
| 5,683,461 A | 11/1997 | Lee et al. | |
| 6,027,742 A | 2/2000 | Lee et al. | |
| 7,501,180 B2 | 3/2009 | Anderson et al. | |
| 7,514,249 B2 | 4/2009 | Gower et al. | |
| 7,544,496 B2 | 6/2009 | Gower et al. | |
| 7,547,449 B2 | 6/2009 | Gower et al. | |
| 8,168,170 B2 | 5/2012 | Myatt | |
| 8,309,134 B2 | 11/2012 | McDonough et al. | |
| 8,747,899 B2 | 6/2014 | Chaput et al. | |
| 8,889,196 B2 | 11/2014 | Xu | |
| 2004/0131562 A1 | 7/2004 | Gower et al. | |
| 2005/0089579 A1 | 4/2005 | Li et al. | |
| 2005/0100559 A1* | 5/2005 | Myatt | A61P 43/00 424/234.1 |
| 2007/0067882 A1 | 3/2007 | Atanasoska et al. | |
| 2008/0241256 A1 | 10/2008 | Kuhn | |
| 2009/0238947 A1* | 9/2009 | Flendrig | A23J 3/08 426/654 |
| 2009/0263497 A1 | 10/2009 | Brito Lopes et al. | |
| 2010/0086618 A1 | 4/2010 | Pashley et al. | |
| 2011/0038921 A1 | 2/2011 | Wen et al. | |
| 2012/0039956 A1 | 2/2012 | Harel et al. | |
| 2013/0195921 A1 | 8/2013 | Bush | |
| 2014/0308332 A1* | 10/2014 | Lynch | A61L 27/54 514/8.2 |
| 2015/0335577 A1* | 11/2015 | Agüeros Bazo | A23K 20/163 424/282.1 |
| 2019/0054012 A1 | 2/2019 | De Pablo et al. | |

FOREIGN PATENT DOCUMENTS

| | | |
|---|---|---|
| CN | 104860284 A | 8/2015 |
| JP | 5158835 B2 | 3/2013 |
| WO | WO 91/11509 | 8/1991 |
| WO | WO-0141821 A1 | 6/2001 |
| WO | WO-03095085 A1 | 11/2003 |
| WO | WO2005/030257 A2 | 4/2005 |
| WO | WO2007/079147 | 7/2007 |
| WO | WO2017/143130 * | 8/2017 |
| WO | WO-2017143130 A1 | 8/2017 |
| WO | WO2017/209823 | 12/2017 |

OTHER PUBLICATIONS

Bisht et al., Current Trends in Biomedical, Engineering & Biosciences, Mar. 21, 2017; 2(2): 1-3. (Year: 2017).*
Sun, Starch Nanoparticles: modifications, toxicity, and drug loading; a thesis presented to the University of Waterloo, 2015. (Year: 2015).*
Neu et al., Biomacromolecules, 2006; 7: 3428-3438 (Year: 2006).*
International Preliminary Report on Patentability issued in PCT Application No. PCT/US18/42063 on dated Jan. 23, 2020.
Extended European Search Report issued in Application No. 18831200.3 on Mar. 13, 2021.
International Search Report and Written Opinion issued in PCT Application No. PCT/US18/42063, dated Sep. 14, 2018.

(Continued)

*Primary Examiner* — Brian Gangle
*Assistant Examiner* — Lakia J Jackson-Tongue
(74) *Attorney, Agent, or Firm* — Weaver Austin Villeneuve & Sampson LLP

(57) ABSTRACT

Provided are freeze-dried (FD) products of biological materials that have improved stability and reduced risk of collapse. The FD products include nanoparticles that are added to formulations including the biological materials prior to freeze-drying. Also described herein are methods of freeze-drying (FD).

16 Claims, 12 Drawing Sheets

(56) References Cited

OTHER PUBLICATIONS

EP Office Action dated Feb. 25, 2022, in Application No. EP18831200.3.
EP Office Action dated Dec. 1, 2022, in Application No. EP18831200.3.
Fukui, et al., "Bio-inspired nanoreactor based on a miniemulsion system to create organic-inorganic hybrid nanoparticles and nanofilms," J. Mater. Chem., 2012, 22, pp. 3493-3499.
Hood, et al. "Synthetic Strategies in the Preparation of Polymer/Inorganic Hybrid Nanoparticles," Materials, 2014, vol. 7, pp. 4057-4087.
International Search Report and Written Opinion, dated Nov. 28, 2017, issued in PCT Application No. PCT/US17/22198.
Qazvini, et al. "Hybrid amorphous nanoparticles composed of calcium phosphate and a cationic polymer," Abstract of Symposium: Hybrid Polymers and Nanocomposites—Oral, 2 pages. Abstract as submitted for ACS Mar. 2016 meeting. Submission date of Oct. 12, 2015. Publication date unknown but after submission date.
Sharma, et al., "An insight into functionalized calcium based inorganic nanomaterials in biomedicine: Trends and transitions," Colloids and Surfaces B: Biointerfaces, No. 133, 2015, pp. 120-139.
Shkilnyy, et al., "Poly(ethylene imine)-Controlled Calcium Phosphate Mineralization," American Chemical Society, Langmuir, vol. 24, 2008, pp. 2102-2109.
U.S. Final office Action dated Jun. 2, 2022 in U.S. Appl. No. 16/084,864.
U.S. Non-Final Office Action dated Oct. 29, 2021 in U.S. Appl. No. 16/084,864.
U.S. Restriction Requirement dated Nov. 20, 2020 in U.S. Appl. No. 16/084,864.
Wang, et al., "Development of injectable organic/inorganic colloidal composite gels made of self-assembling gelatin nanospheres and calcium phosphate nanocrystals," Acta Biomaterialia, vol. 10, 2014, pp. 508-519.
Zhao, X. et al. "Calcium Phosphate Hybrid Nanoparticles: Self-Assembly Formation, Characterization, and Application as an Anticancer Drug Nanocarrier," Chem. Asian J., 2013, vol. 8, pp. 1306-1312.
Bell, L., "Kinetics of Non-enzymatic Browning in Amorphous Solid Systems: Distinguishing the Effects of Water Activity and the Glass Transition", Food Research International, 1996, vol. 28(6), pp. 591-597.
Brenner, M., et al., "The Utility of Probiotics in the Treatment of Irritable Bowel Syndrome: a Systematic Review", Am J Gastroenterol, 2009, vol. 104, pp. 1033-1049.
Cogan, T., et al., "Characterization of the Lactic Acid Bacteria in Artisanal Dairy Products", Journal of Dairy Research, 1997, vol. 64(3), pp. 409-421.
Ekdawi-Sever, N., et al., "Effects of Annealing on Freeze-dried Lactobacillus Acidophilus", Journal of Food Science, 2003, vol. 68(8), pp. 2504-2511.
Elias, L., et al., "Morphology and Rheology of Immiscible Polymer Blends Filled With Silica Nanoparticles", Polymer, 2007, vol. 4820), pp. 6029-6040.
Epple, M., et al., "Application of Calcium Phosphate Nanoparticles in Biomedicine", Journal of Materials Chemistry, 2010, vol. 20, pp. 18-23.
Garcia, N., et al., "Effect of Glycerol on the Morphology of Nanocomposites Made From Thermoplastic Starch and Starch Nanocrystals", Carbohydrate Polymers, 2011, vol. 84, pp. 203-210.
Hadjicharalambous, C., et al., "Calcium Phosphate Nanoparticles Carrying BMP-7 Plasmid DNA Induce an Osteogenic Response in MC3T3-E1 Pre-osteoblasts", Journal of Biomedical Materials Research, 2015, vol. 103A(12), pp. 3834-3842.
Kulkarni, D., et al., "Temperature Dependent Rheological Property of Copper Oxide Nanoparticles Suspension (Nanofluid)", Journal of Nanoscience and Nanotechnology, 2006, vol. 6, pp. 1150-1154.
Lecorre, D., et al., "Preparation and Application of Starch Nanoparticles for Nano Composites:a Review", Reactive &Functional Polymers, 2014, vol. 85, pp. 97-120.
Lecorre, D., et al., "Starch Nanoparticles: a Review", Biomacromolecules, 2010, vol. 11, pp. 1139-1153.
Lee, M., et al., "Target-specific Delivery of Sirna by Stabilized Calcium Phosphate Nanoparticles Using Dopa-hyaluronic Acid Conjugate", Journal of Controlled Release, 2014, vol. 192, pp. 122-130.
Leroy, F., et al., "Lactic Acid Bacteria as Functional Starter Cultures for the Food Fermentation Industry", Trends in Food Science & Technology, 2004, vol. 15(2), pp. 67-78.
Li, M., et al., "Cellulose Nanoparticles: Structure-Morphology-Rheology Relationships", ACS Sustainable Chemistry & Engineering, 2015, vol. 3(5), pp. 821-832.
Mi, P., et al., "Hydrothermally Synthesized PEGylated Calcium Phosphate Nanoparticles Incorporating Gd-DTPA for Contrast Enhanced MRI Diagnosis of Solid Tumors", Journal of Controlled Release, 2014, vol. 174, pp. 63-71.
Moayyedi, P., et al., "The Efficacy of Probiotics in the Treatment of Irritable Bowel Syndrome: a Systematic Review", Gut, 2010, vol. 59(3), pp. 325-332.
Mostaghaci, B., et al., "Calcium Phosphate System for Gene Delivery: Historical Background and Emerging Opportunities", Current Pharmaceutical Design, 2016, vol. 22(11), pp. 1529-1533.
Nail, S., et al., "Freeze-drying: Principles and Practice", Pharmaceutical Dosage Forms : Parenteral Medications, 1993, vol. 2, pp. 162-233.
Nejadnik, M., et al., "Self-healing Hybrid Nanocomposites Consisting of Bisphosphonated Hyaluronan and Calcium Phosphate Nanoparticles", Biomaterials, 2014, vol. 35(25), pp. 6918-6929.
Pakdaman, M., et al., "The Effects of the Dds-1 Strain of Lactobacillus on Symptomatic Relief for Lactose Intolerance—a Randomized, Double-blind, Placebo-controlled, Crossover Clinical Trial", Nutrition Journal, 2016, vol. 15(56), pp. 2-11.
Reiff, C., et al., "Inflammatory Bowel Disease, Gut Bacteria and Probiotic Therapy", International Journal of Medical Microbiology, 2010, vol. 300(1), pp. 25-33.
Santander-Ortega, M., et al., "Nanoparticles Made From Novel Starch Derivatives for Transdermal Drug Delivery", Journal of Controlled Release, 2010, vol. 141, pp. 85-92.
Schilling, C., et al., "Rheology of Alumina-nanoparticle Suspensions: Effects of Lower Saccharides and Sugar Alcohols", Journal of the European Ceramic Society, 2002, vol. 22(6), pp. 917-921.
Schneider, O., et al., "Light-curable Polymer/calcium Phosphate Nanocomposite Glue for Bone Defect Treatment", Acta Biomaterialia, 2010, vol. 6, pp. 2704-2710.
Shen, J., et al., "Effect of Probiotics on Inducing Remission and Maintaining Therapy in Ulcerative Colitis, Crohn's Disease, and Pouchitis: Meta-analysis of Randomized Controlled Trials", Inflamm Bowel Dis, 2014, vol. 20(1), pp. 21-35.
Simi, K., et al., "Hydrophobic Grafted and Cross-linked Starch Nanoparticles for Drug Delivery", Bioprocess Biosyst Eng, 2007, vol. 30, pp. 173-180.
Sisson, G., et al., "Randomised Clinical Trial: a Liquid Multi-strain Probiotic vs. Placebo in the Irritable Bowel Syndrome—a 12 Week Double-blind Study", Alimentary Pharmacology and Therapeutics, 2014, vol. 40(1), pp. 51-62.
Studart, R., et al., "Rheology of Concentrated Suspensions Containing Weakly Attractive Alumina Nanoparticles", The American Ceramic Society, 2006, vol. 89(8), pp. 2418-2425.
Tseng, W., et al., "Rheology and Colloidal Structure of Aqueous TiO2 Nanoparticle Suspensions", Materials ScienceandEngineering, 2003, vol. 355(1-2), pp. 186-192.
U.S. Non-Final Office Action dated Apr. 27, 2023, in U.S. Appl. No. 16/084,864.
Uskokovic, V., et al., "Phase Composition Control of Calcium Phosphate Nanoparticles for Tunable Drug Delivery Kinetics and Treatment of Osteomyelitis. Preparation and Drug Release", Journal of Biomedical Materials Research, 2013, vol. 101A(5), pp. 1416-1426.

(56) References Cited

OTHER PUBLICATIONS

Van, T., et al., "Injectable Hydrogel Composite Based Gelatin-PEG and Biphasic Calcium Phosphate Nanoparticles for Bone Regeneration", Journal of Electronic Materials, 2016, vol. 45(5), pp. 2415-2422.

Vonk, R., et al., "Probiotics and Lactose Intolerance", InTech Open Science, 2012, vol. 7, pp. 149-160.

Wang, P., et al., "Bone Tissue Engineering via Nanostructured Calcium Phosphate Biomaterials and Stem Cells", Bone Research, 2014, vol. 2, pp. 1-13.

Wang, X., et al., "Designed Synthesis of Lipid-Coated Polyacrylic Acid/Calcium Phosphate Nanoparticles as Dual pH-Responsive Drug-Delivery Vehicles for Cancer Chemotherapy", Chemistry European Journal, 2017, vol. 23, pp. 6586-6595.

Zhang, Z., et al., "Facile Preparation of Corn Starch Nanoparticles by Alkali-freezing Treatment", The Royal Society of Chemistry, 2013, vol. 3, pp. 13406-13411.

Zhao, R., et al., "Emerging Biodegradable Materials: Starch- and Protein-based Bio-nanocomposites", Journal Mater Science, 2008, vol. 43, pp. 3058-3071.

Abraham, B., et al., "Prebiotics and Probiotics in Infl ammatory Bowel Disease (IBD)", A.N. Ananthakrishnan (ed.), Nutritional Management of Infl ammatory Bowel Diseases, 2016, vol. 8, pp. 131-147.

Alfaro-Perez, J., et al., "Preservation of Biological Materials for Long-term Storage", Novel Aggressive Freeze-drying Protocols to Preserve Biological Materials the University of Chicago, 2017, vol. 1, pp. 1-153.

* cited by examiner

Control

Sample with CaP nanoparticles

Sample with starch nanoparticles

Control

Sample with CaP nanoparticles

Sample with starch nanoparticles

FREEZE-DRIED FORMULATIONS INCLUDING NANOPARTICLES AND METHODS OF FREEZE-DRYING

CROSS-REFERENCE TO RELATED APPLICATION

This application claims priority to U.S. Provisional Patent Application No. 62/532,502, dated Jul. 14, 2017, which is incorporated by reference herein in its entirety and for all purposes.

FIELD OF INVENTION

This disclosure relates to formulations and methods for preserving biological materials and more particularly to formulations and methods for preserving bacteria.

BACKGROUND

Assuring the survival of bacteria after their manufacturing poses a challenge. Freeze-drying (FD), which allows bacteria to survive by lowering the water content of the final product, provides one solution. However, freeze-drying methods have various challenges. Existing FD protocols face problems related to deformation of the product during freeze-drying. This is referred to as collapse. Certain FD protocols also result in faster than desirable decay.

SUMMARY

Described herein are freeze-dried (FD) products of biological materials that have improved stability and reduced risk of collapse. The FD products include nanoparticles that are added to formulations including the biological materials prior to freeze-drying. Also described herein are methods of freeze-drying (FD).

One aspect of the disclosure relates to a composition that includes a biological material; a polyhydroxyl compound; and nanoparticles, wherein the composition is freeze-dried. In some embodiments, the composition further includes phosphate ions. Examples of nanoparticles include polymer-stabilized calcium phosphate nanoparticles and starch nanoparticles. Examples of polyhydroxyl compounds include a monosaccharide, a disaccharide, or a polysaccharide. In some embodiments, the polyhydroxyl compound is trehalose. In some embodiments, the biological material is a microorganism. In some embodiments, the biological material is a lactic acid bacteria. In some embodiments, the biological material is a probiotic. In some embodiments, water in the composition is concentrated in the nanoparticles.

In some embodiments, the water activity $a_w$ of the freeze-dried composition is less than 0.2 or less than 0.15.

Another aspect of the disclosure relates to a composition that includes a biological material; a polyhydroxyl compound; and nanoparticles, wherein the composition is an aqueous solution. In some embodiments, the composition further includes phosphate ions. Examples of nanoparticles include polymer-stabilized calcium phosphate nanoparticles and starch nanoparticles. Examples of polyhydroxyl compounds include a monosaccharide, a disaccharide, or a polysaccharide. In some embodiments, the polyhydroxyl compound is trehalose. In some embodiments, the biological material is a microorganism. In some embodiments, the biological material is a lactic acid bacteria. In some embodiments, the biological material is a probiotic. In some embodiments, water in the composition is concentrated in the nanoparticles. In some embodiments, the nanoparticles constitute between 1-5% by weight of the aqueous solution.

Another aspect of the disclosure relates to a composition that includes a biological material; a polyhydroxyl compound; and nanoparticles, wherein the composition is a solid-state mixture. In some embodiments, the composition further includes phosphate ions. Examples of nanoparticles include polymer-stabilized calcium phosphate nanoparticles and starch nanoparticles. Examples of polyhydroxyl compounds include a monosaccharide, a disaccharide, or a polysaccharide. In some embodiments, the polyhydroxyl compound is trehalose. In some embodiments, the biological material is a microorganism. In some embodiments, the biological material is a lactic acid bacteria. In some embodiments, the biological material is a probiotic. In some embodiments, water in the composition is concentrated in the nanoparticles.

Another aspect of the disclosure relates to a method that includes mixing a biological material, a polyhydroxyl compound, and nanoparticles in an aqueous solution; drying the aqueous solution to form a solid; and performing a freeze-drying (FD) protocol to sublimate ice crystals in the solid and form a freeze-dried product. Examples of nanoparticles include polymer-stabilized calcium phosphate nanoparticles and starch nanoparticles. Examples of polyhydroxyl compounds include a monosaccharide, a disaccharide, or a polysaccharide. In some embodiments, the polyhydroxyl compound is trehalose. In some embodiments, the biological material is a microorganism. In some embodiments, the biological material is a lactic acid bacteria. In some embodiments, the biological material is a probiotic.

These and other aspects are described below with reference to the drawings.

DETAILED DESCRIPTION

Figure 1A:
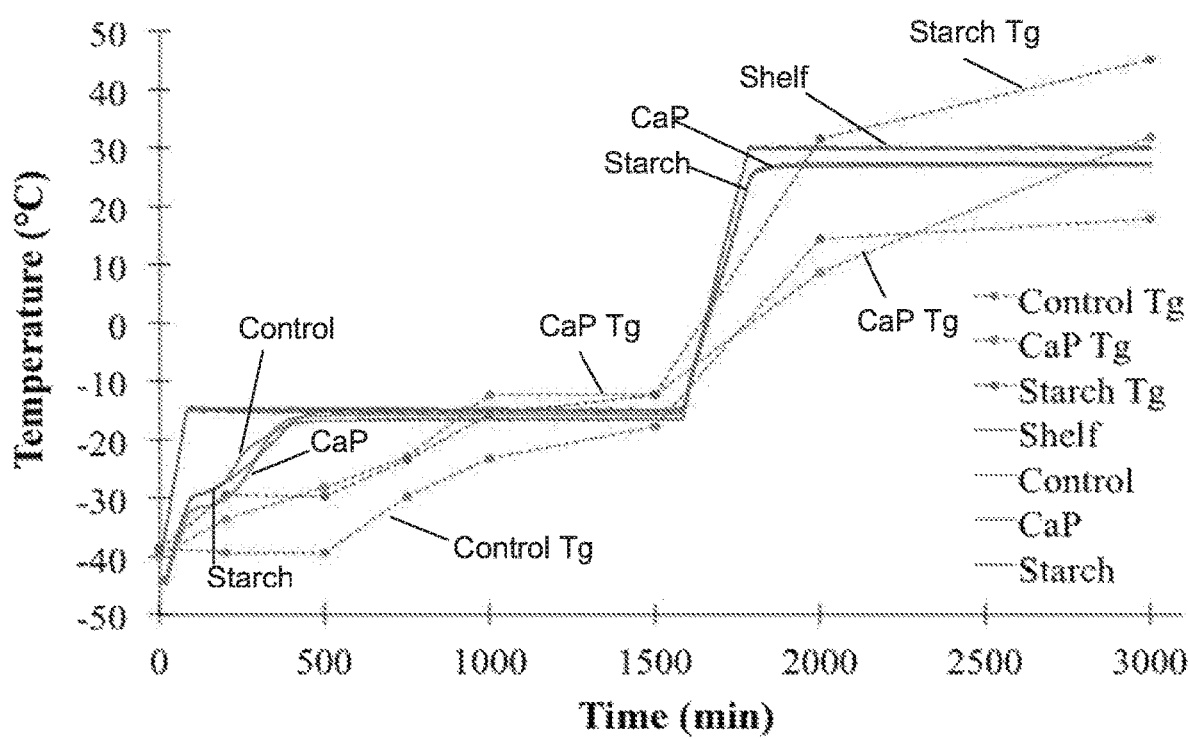
FIG. 1(a) is a graph (temperature vs time) characterizing a freeze-drying (FD) protocol for a control sample, a sample with starch nanoparticles, and a sample with CaP nanoparticles.

Described herein are freeze-dried (FD) products of biological materials that have improved stability and reduced risk of collapse. The FD products include nanoparticles that are added to formulations including the biological materials prior to freeze-drying. Also described herein are methods of freeze-drying (FD).

While most of the description below is presented in terms of FD products of lactic acid bacteria (LAB) and related FD methods, it is not so limited. The FD products may include any biological material, including blood, bacteria and other microorganisms and cells, body tissues, enzymes, food products, nucleic acids, organs, proteins, semen, vaccines, vesicles, and viruses. In particular applications, the FD products may include microorganisms used in foods and probiotics, with examples including *Lactobacillus* and *Bifidobacterium*, as well as yeasts such as *Saccharomyces*.

Lactic acid bacteria (LAB) represent industrially important microorganisms with multiple applications. Some strains are commercially available as culture starters for cheese and yogurt, while other strains are used in probiotics that provide various health benefits. Probiotics may be used in, for example, the treatment of irritable bowel syndrome, inflammatory bowel disease, and lactose intolerance. FD is a technique that reduces the water content of the bacterial product so that a stable product with good potency will reach the customer. FD protocols use low temperatures and vacuum pressures, conditions that help to prevent degradation of thermolabile materials, such as bacteria, which would otherwise become unviable using other drying processes. Current industrial FD processing of LAB typically differs from that of pharmaceutical products. For LAB, the freezing step typically takes place out of the freeze-dryer, with the bacterial solution dripped over liquid nitrogen in order to produce spherical pellets. The pellets are then transferred to a freeze-dryer to remove ice crystals through sublimation. During drying, most pellets remain cold and their initial shape is retained. However, in some cases, a deformation or loss of the original shape occurs, which is also known as collapse.

In the products and methods described herein, nanoparticles are preferably incorporated into the bacterial (or other biological material) formulation prior to freeze-drying. In some embodiments, the nanoparticles increase the viscosity of the solution to be freeze-dried. This allows the primary drying step to be conducted more efficiently, reducing occurrence of collapse.

For food-related applications, the nanoparticles are biocompatible and compatible with the biological material being preserved, and may be Generally Recognized as Safe (GRAS) as described by the U.S. Food & Drug Administration. Examples include starch nanoparticles, cellulose nanoparticles, certain polymeric nanoparticles, calcium phosphate nanoparticles, and calcium carbonate nanoparticles. In some embodiments, polymer-stabilized calcium phosphate (CaP) nanoparticles, discussed further below, are used.

In some embodiments, the nanoparticles are hygroscopic. The hygroscopic nanoparticles may act as water sinks that reduce the interaction of free water with bacteria. Ambient moisture can interact with the saccharides in freeze-dried products to induce non-enzymatic Maillard reactions causing browning and ultimately leading to cellular death. By trapping water, hygroscopic nanoparticles prevent its contact with bacteria, improving the physical properties and the long-term stability of the bacteria.

As used herein, the term "nanoparticle" refers to a particle, the largest dimension of which is less than 1 μm. The term "nanosphere" refers to a generally spherical particle, the largest dimension of which is less than 1 Nanospheres are distinct from needle-like and other non-spherical formations, however it is understood that nanospheric particles disclosed herein may deviate from perfect spheres. It should be noted that although the below discussion refers chiefly to nanoparticles, in some embodiments, particles having sizes greater than 1 μm may be used in the methods and compositions described herein.

In addition to the biological material and the nanoparticles, the freeze-dried products may contain components including cryoprotectants, water, salts, and buffer. Examples of cryoprotectants include trehalose and other saccharides (e.g., monosaccharides, disaccharides, or polysaccharides). In some embodiments, the freeze-dried products include a polyhydroxyl compound (e.g., a disaccharide) and phosphate ions as described in U.S. Pat. No. 6,653,062, which is incorporated by reference herein for description of components of a freeze-dried product and intermediates thereof.

Also provided are aqueous solutions suitable for freeze-drying. The aqueous solutions may include the biological material and nanoparticles as well as a cryoprotectant. In some embodiments, it contains phosphate ions and a polyhydroxyl compound. Also provided are solid compositions, suitable for reconstitution into an aqueous solution and freeze-drying. The solid compositions may include the biological material and nanoparticles as well as a cryroprotectant. In some embodiments, it contains phosphate ions and a polyhydroxyl compound.

Also provided are methods for freeze-drying. The methods involve mixing the biological material in a solution with nanoparticles followed by freeze-drying. In some embodiments, the solution including the nanoparticles is frozen outside of a freeze-dryer. Liquid nitrogen may be used to freeze the solution; for example, the solution may be dripped over liquid nitrogen to form spherical pellets. Ice crystals may then be removed in a freeze-dryer by sublimation.

Drying may include a primary drying and secondary drying step. In some embodiments, the primary drying step includes two temperature ramps. In some embodiments, the secondary drying step includes a hold at a secondary drying temperature.

FIG. 1(a) is a graph characterizing a FD protocol for a control sample, a sample with starch nanoparticles, and a sample with CaP nanoparticles. The glass transition temperatures of the control sample, the starch nanoparticle sample, and the CaP nanoparticle sample are shown in dotted lines. The shelf temperature is also shown. Each sample includes multiple pellets fabricated as described below in the Examples. The product temperature profiles (solid lines) were generated from thermocouple measurements and the $T_g$ profile from differential scanning calorimetry (DSC).

Figure 1B:
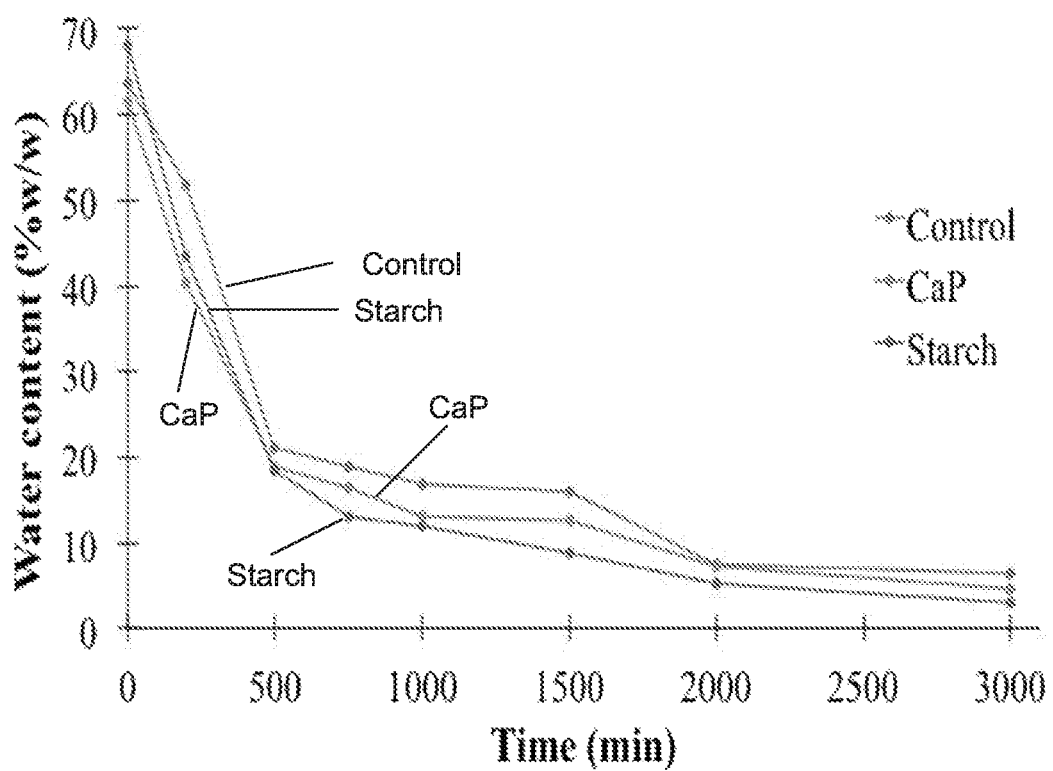
FIG. 1(b) shows water content profile during the FD protocol shown in FIG. 1(a).

The freeze-drying (FD) cycle at 100 mTorr shown in FIG. 1(a) includes a quick ramp to −17° C., a prolonged holding step at that temperature, a quick ramp to 30° C. and a secondary drying step at the latter temperature. The pellets obtained with this FD cycle were characterized as shown in Table 1. FIG. 1(b) shows water content profile during the FD protocol shown in FIG. 1(a).

TABLE 1

Properties of the freeze-dried pellets after completion of a FD protocol

| Sample | Tg (° C.) | Water content (% w/w) | Water activity, $a_w$ |
|---|---|---|---|
| Control | 17.8 | 6.4 | 0.291 |
| 2 wt % Calcium phosphate NPs | 31.9 | 4.6 | 0.196 |
| 2 wt % Starch NPs | 45.1 | 2.9 | 0.134 |

Figure 2:
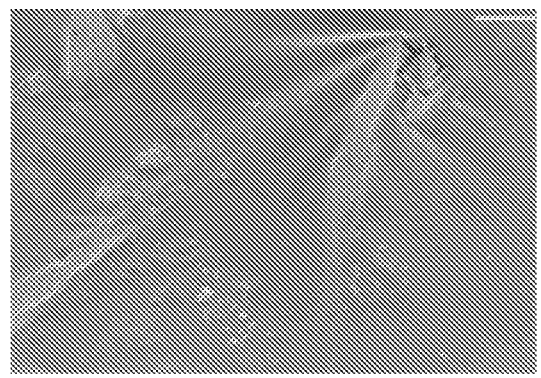
FIG. 2 shows scanning electron microscope (SEM) images of freeze-dried pellets after the completion of the FD shown in FIG. 1(a).
Figure 2:
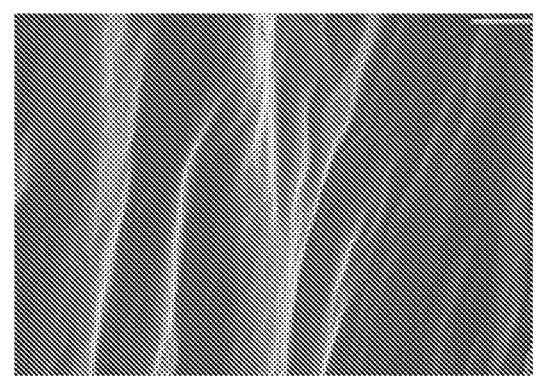
Figure 2:
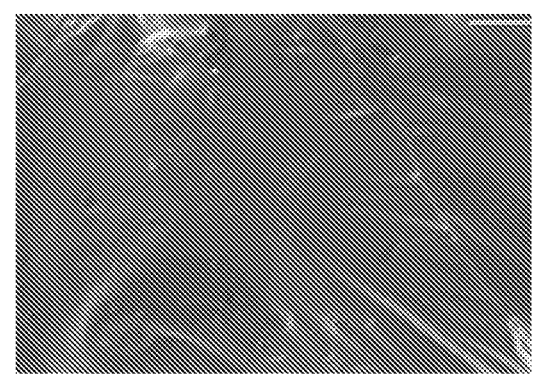

For the control pellets (no nanoparticles), most pellets were obtained devoid of collapse, but some of them (around 20%) were connected to one another or presented some bubbles. The water content and water activity ($a_w$) of the control were very high, which suggests that amorphous water is very difficult to remove during secondary drying. As a reference, for most pellets in manufacturing, $a_w$ is usually kept below 0.10 to assure low water content and optimal survival rates. The $a_w$ of the control pellets are far above the industrial standard and were expected to render poor performance. As shown in FIG. 1(a), the product temperature ($T_p$) of the control sample (solid line) was above the glass transition temperature ($T_g$) (dotted line), with a maximum difference of 25° C. FIG. 1(b) shows that sublimation of ice crystals occurs as fast in the control sample as in the samples with nanoparticles, but the control sample retains more water throughout all secondary drying. FIG. 2 shows scanning electron microscope (SEM) images of freeze-dried pellets after the completion of the FD shown in FIG. 1(a). Scale bar is 2 μm. The SEM image of control pellets reveals a microstructure that is mostly continuous, i.e., it lacks pores, which explains why it is so difficult to remove "trapped" amorphous water during the secondary drying stage of the process. This phenomenon is critical in semi-collapsed pellets.

The pellets with 2 wt % of calcium phosphate (CaP) nanoparticles (NPs) (average size of 300 nm) were almost free of collapse, but some of them displayed some connectivity. Collapse was avoided in more than 95% of the pellets. This may be due to the expected higher viscosity due to the presence of NPs. The freeze-dried pellets had a higher glass transition temperature (Tg) than the control sample, and subsequently lower residual water content and $a_w$. FIG. 1(a) reveals that during most of the primary drying stage of the cycle $T_p$ is higher than $T_g$ for the CaP nanoparticle sample, but the trend switches at around 1000 minutes. However, during secondary drying water desorption is not very efficient (FIG. 1(b)) leading to a product with high $a_w$. The SEM image in FIG. 2 depicts a similar microstructure compared to control pellets, which seems to imply that the microstructure is not being affected by the presence of the NPs, but rather the NPs are distributed within the glassy matrix that supports the pellet.

The pellets with 2 wt % of starch NPs (average size of 85 nm) were completely devoid of collapse. The pellets had the highest $T_g$, as well as the lowest residual water content and $a_w$. During primary drying the $T_g$ and $T_p$ profiles were very similar compared to the 2 wt % CaP NPs sample (FIG. 1(a)), but water removal during secondary drying was more efficient, which allowed a simultaneous rapid increase of $T_g$ and decrease of water content. The SEM image in FIG. 2 reveals a similar microstructure than the control sample, supporting the hypothesis that the NPs are being distributed within the matrix without causing any structural changes.

Figure 3A:
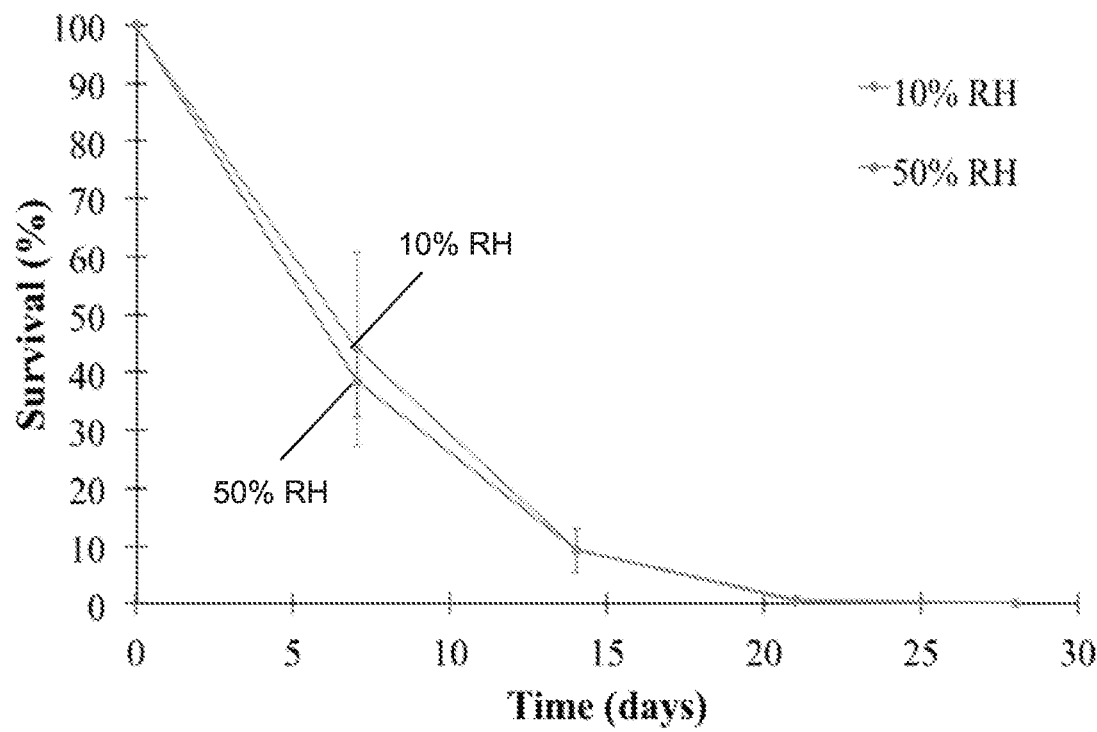
FIG. 3(a) shows bacterial survival as function of time in the incubator for 10% relative humidity (RH) and for 50% RH for an accelerated decay test of the control sample after the FD protocol in FIG. 1(a) was performed.
Figure 3B:
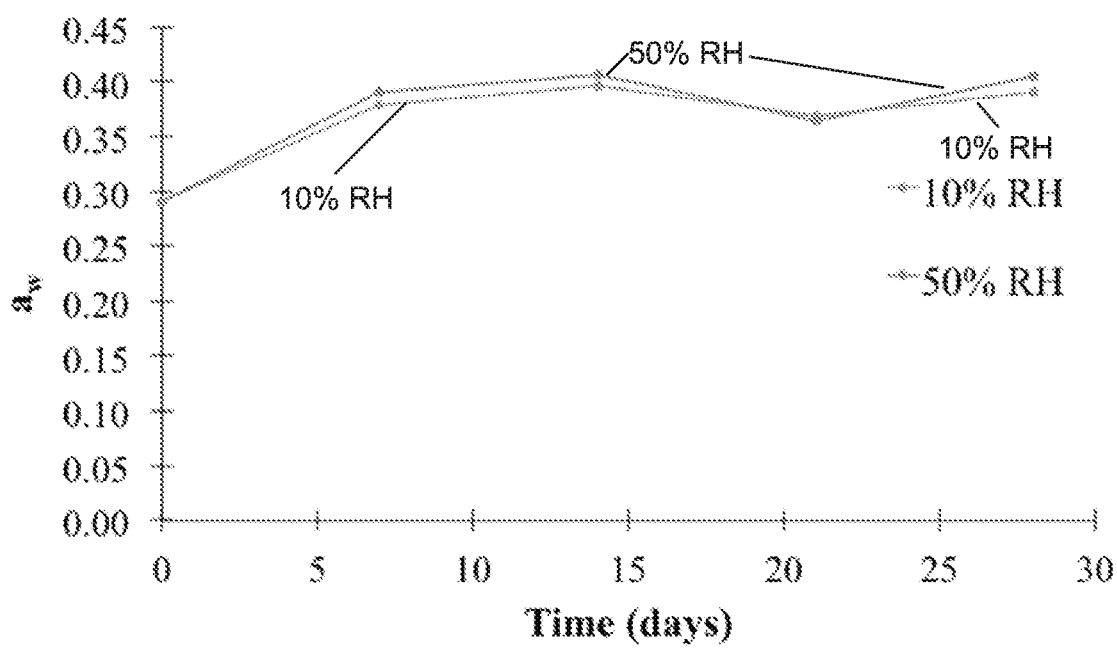
FIG. 3(b) shows water activity ($a_w$) as function of time in the incubator for 10% RH and for 50% RH.

An accelerated decay test of the control sample after the FD protocol in FIG. 1(a) was performed. Pellets were placed inside chambers at different controlled humidity and stored in an incubator at 38° C. The pellets were later retrieved at different times to quantify their survival rate and $a_w$. FIG. 3(a) shows bacterial survival as function of time in the incubator for 10% RH and 50% RH. FIG. 3(b) shows $a_w$ as function of time in the incubator for 10% RH and 50% RH.

FIGS. 3(a) and 3(b) show that the control sample decays very quickly with uptake of a significant amount water that increases almost 0.1 units of $a_w$ during the first 7 days. Furthermore, the pellets started to show signs of browning which indicates the occurrence of Maillard reactions and degradation of the glassy matrix.

Figure 4A:
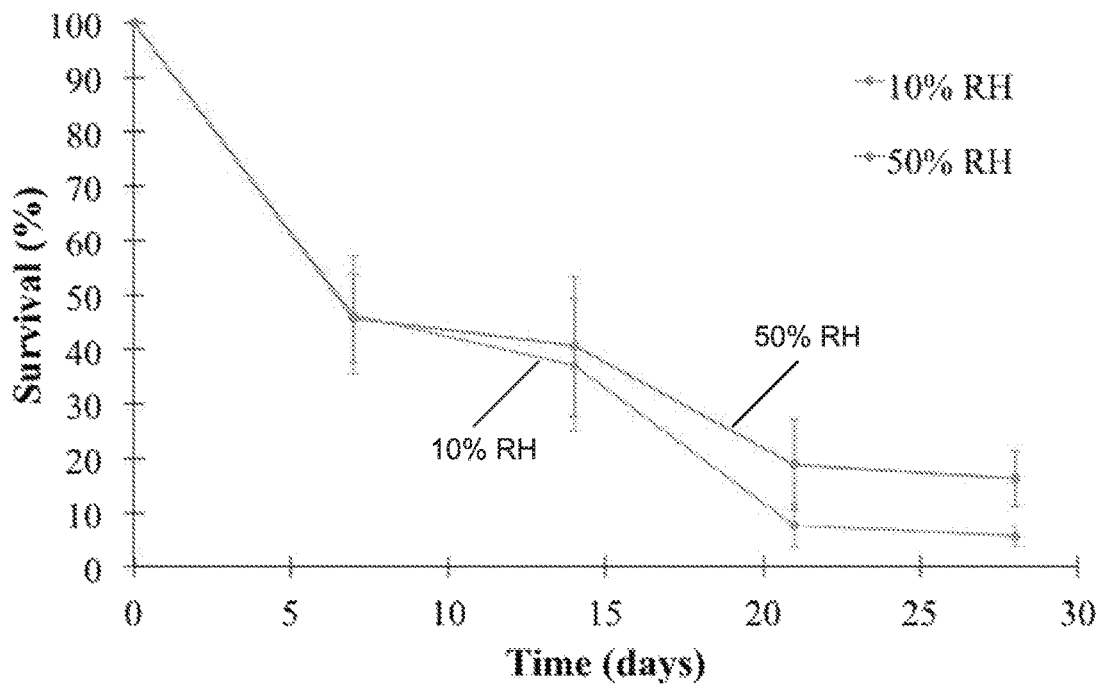
FIG. 4(a) shows bacterial survival as function of time in the incubator for 10% RH and 50% RH for an accelerated decay test of a sample with 2 wt % calcium phosphate (CaP) nanoparticles (NPs).
Figure 4B:
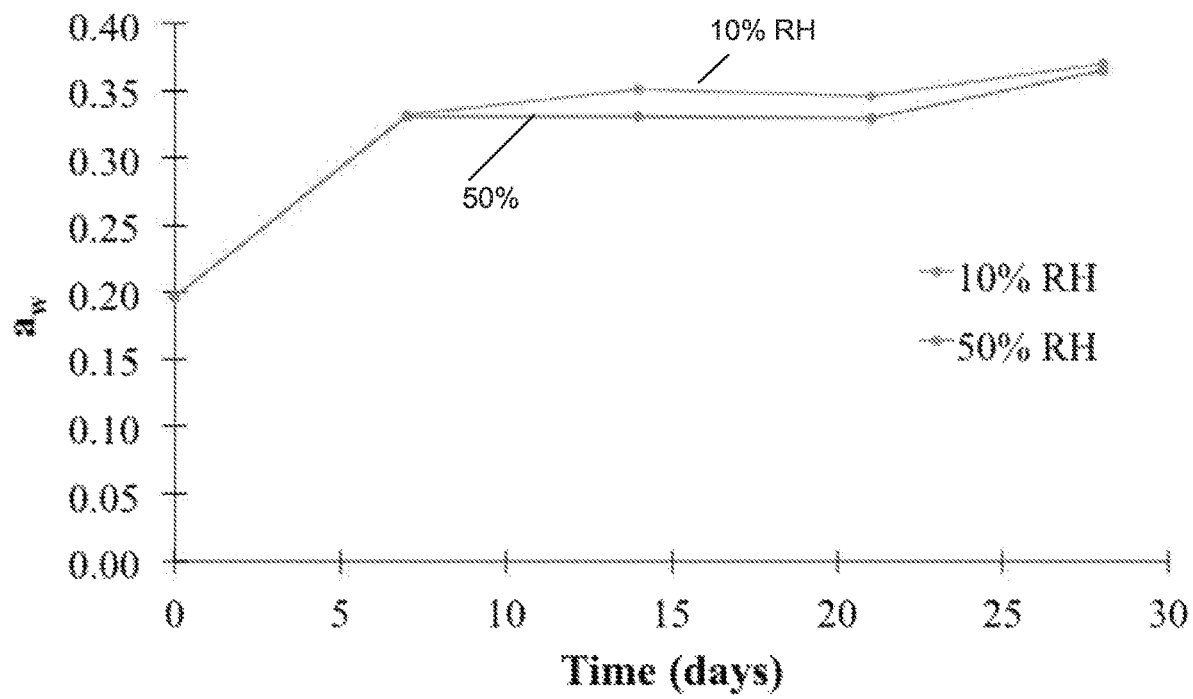
FIG. 4(b) shows $a_w$ as function of time in the incubator for 10% RH and 50% RH.

Samples with NPs showed improved stability compared to control. FIGS. 4(a) and 4(b) shows results of an accelerated decay test of the 2 wt % CaP NPs sample. FIG. 4(a) shows bacterial survival as function of time in the incubator for 10% RH and 50% RH. FIG. 4(b) shows $a_w$ as function of time in the incubator for 10% RH and 50% RH. The CaP NP sample retained a survival rate of almost 20% at 50% RH conditions after 28 days (FIG. 4(a)), whereas the control sample exhibited complete loss of bacterial survival. Even though the increase of $a_w$ is more than 0.1 units, the final stability is higher than in the control sample. This could indicate that a lot of water is being absorbed by the NPs during the first days in the incubator, retarding the contact of free water with bacteria. A modified cycle for a sample with CaP NPs is discussed further below.

Figure 5A:
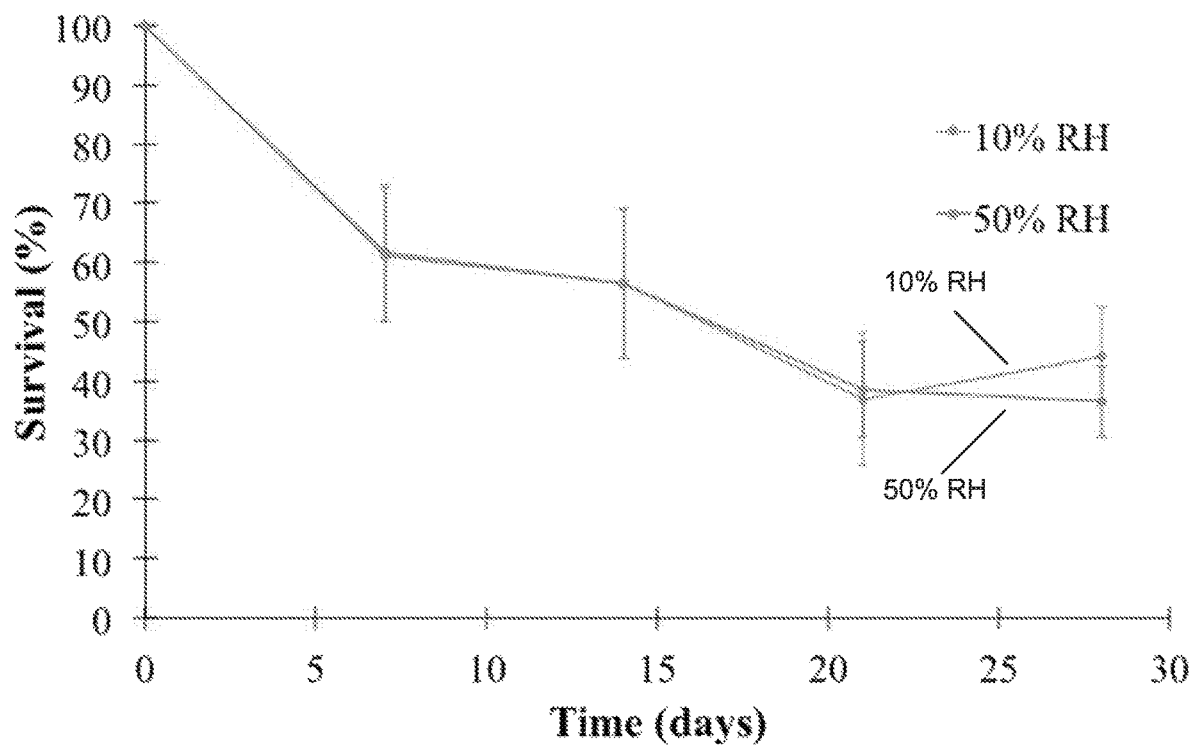
FIG. 5(a) shows bacterial survival as function of time in the incubator for 10% RH and 50% RH for an accelerated decay test of a sample with 2 wt % starch NPs.
Figure 5B:
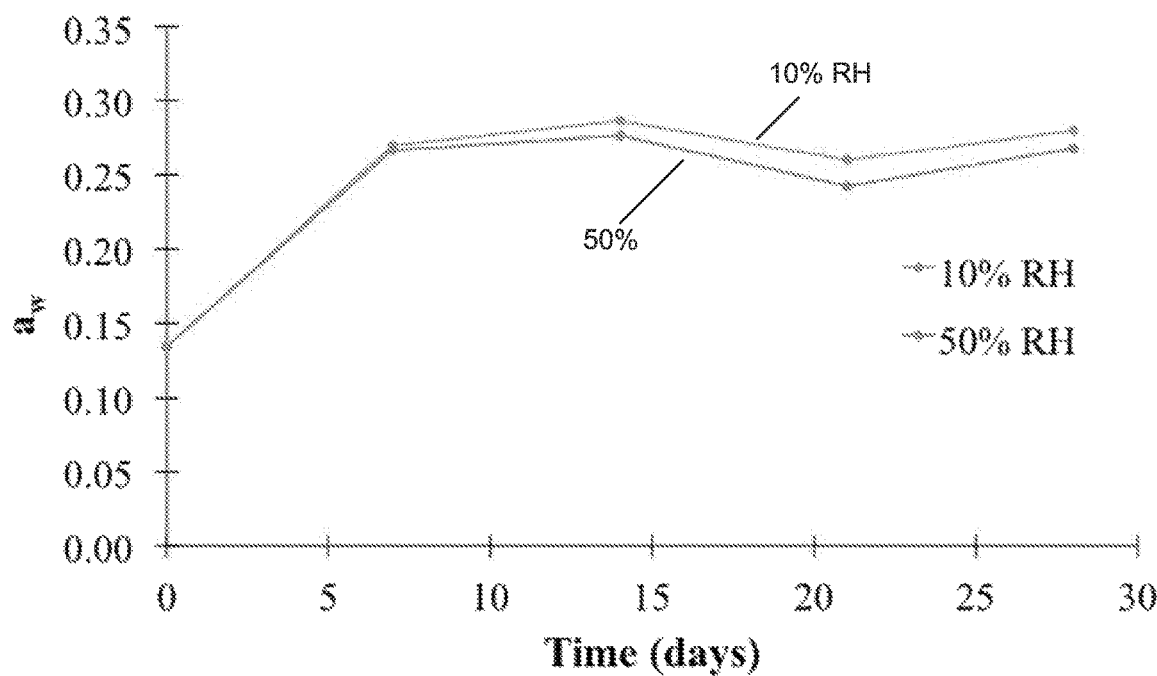
FIG. 5(b) shows $a_w$ as function of time in the incubator for 10% RH and 50% RH.

The sample with 2 wt % of starch NPs exhibited the best survival rate with the FD cycle shown in FIG. 1(a). FIGS. 5(a) and 5(b) shows results of an accelerated decay test of the 2 wt % starch NPs sample. FIG. 5(a) shows bacterial survival as function of time in the incubator for 10% RH and 50% RH. FIG. 5(b) shows $a_w$ as function of time in the incubator for 10% RH and 50% RH. The survival profile against time of decay shows an improved stability for every day in which measurements were made, as well as a final survival rate (28 days) of approximately 45%. The survival may be favorable due to an initial lower value of $a_w$, despite the same increase of 0.1 units after 7 days as exhibited with the control sample. The starch NPs pellets did not present any type of browning during the whole duration of the experiments.

As indicated above, a modified FD cycle was performed for a sample with 2 wt % CaP NPs. The modified cycle included a longer ramping step and an extended secondary drying step as compared to the initial FD cycle described with respect to FIG. 1(a). Table 2 shows the results.

TABLE 2

Cycle modification to the initial FD protocol: extension of ramp and secondary drying steps. Physical properties of FD pellet (2 wt % CaP NP) after completion of protocol and bacterial survival after 7 days in the incubator at 38° C.

| FD protocol | Time = 0 days | Time = 7 days 10% RH | Time = 7 days 50% RH |
| --- | --- | --- | --- |
| Initial FD cycle | $T_g$ = 31.9° C. W.C. = 4.6% $a_w$ = 0.196 | Survival = 46.2 ± 10.8% $a_w$ = 0.332 | Survival = 45.6 ± 8.1% $a_w$ = 0.331 |
| Modified FD cycle with extended steps | $T_g$ = 32.9° C. W.C. = 4.2% $a_w$ = 0.136 | Survival = 59.4 ± 10.3% $a_w$ = 0.288 | Survival = 53.3 ± 14.5% $a_w$ = 0.287 |

The residual water content and $T_g$ did not change dramatically, however the initial $a_w$ value was significantly reduced. After 7 days in the incubator, the survival of bacteria was improved by 30% at 10% HR conditions, despite a similar increase in $a_w$ of 0.15 units. This provides evidence that the uptake of water by the nanoparticles do not impact negatively the survival of bacteria. Lower initial values of $a_w$ can improve the survival of samples that have 2 wt % of calcium phosphate nanoparticles.

Figure 6:
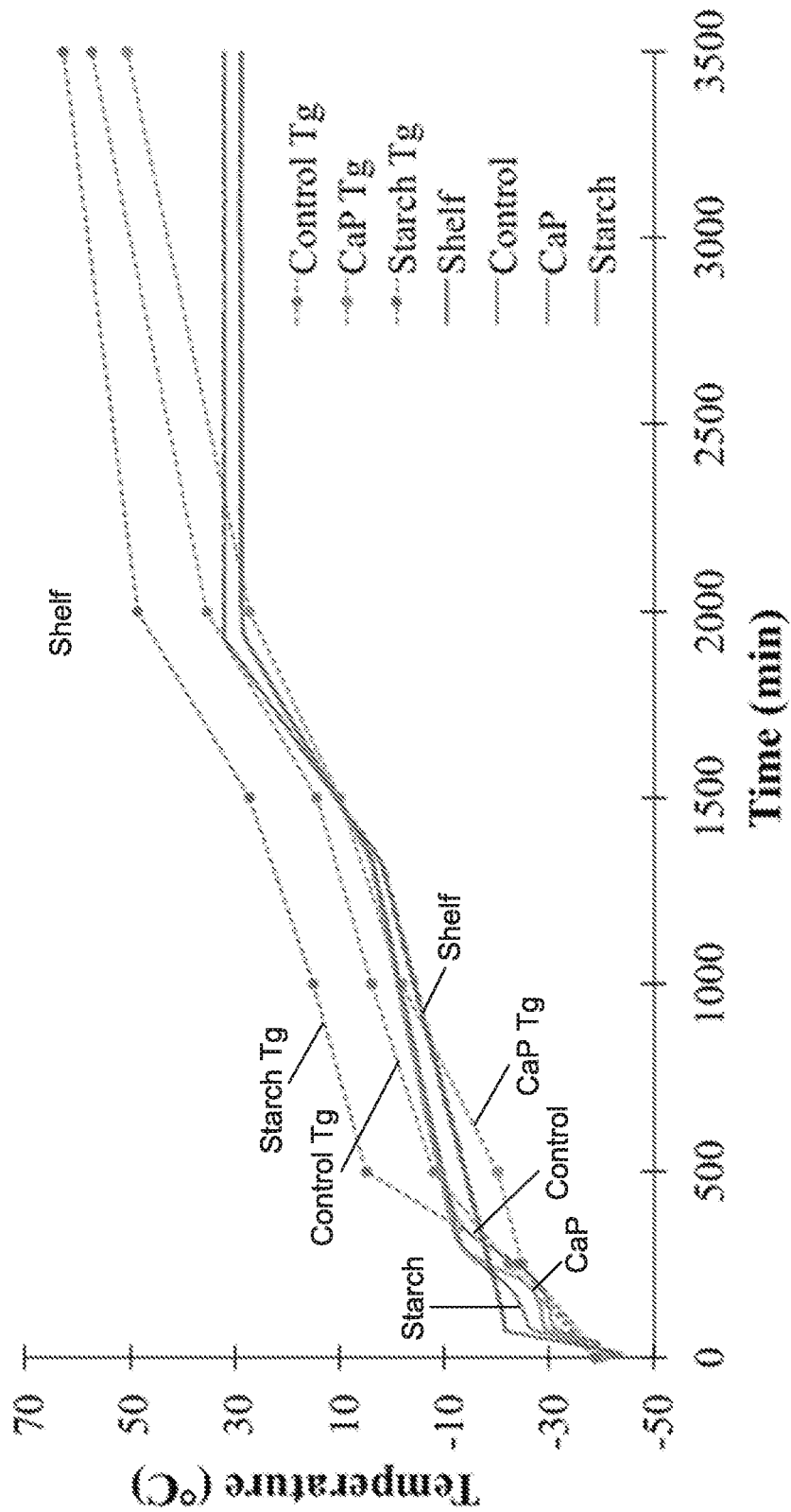
FIG. 6 depicts a FD cycle that is more conservative than that depicted in FIG. 1(a) as well as the temperature ($T_p$) profiles for control, 2 wt % starch NP, and 2 wt % CaP NP samples.

The water activity may be lowered using a more conservative FD cycle as shown above in Table 2. FIG. 6 depicts a FD cycle that is more conservative than that depicted in FIG. 1(a) as well as the temperature ($T_p$) profiles for control, 2 wt % starch NP, and 2 wt % CaP NP samples. In all cases, $T_p$ increases rapidly toward the shelf temperature during primary drying and no signs of collapse are observed for any of the FD pellets (Table 3). In every case, $T_g$ was higher and $a_w$ was lower than in the initial FD cycle. In contrast with the initial FD cycle, the pellets with NPs obtained with this cycle have higher $a_w$ and residual water content than the control pellets.

TABLE 3

Properties of the freeze-dried pellets after completion of a conservative FD protocol

| Sample | $T_g$ (° C.) | Water content (% w/w) | Water activity, $a_w$ |
| --- | --- | --- | --- |
| Control | 57.2 | 1.3 | 0.076 |
| 2 wt % Calcium phosphate NPs | 50.5 | 6.9 | 0.107 |
| 2 wt % Starch NPs | 62.8 | 4.8 | 0.095 |

Figure 7:
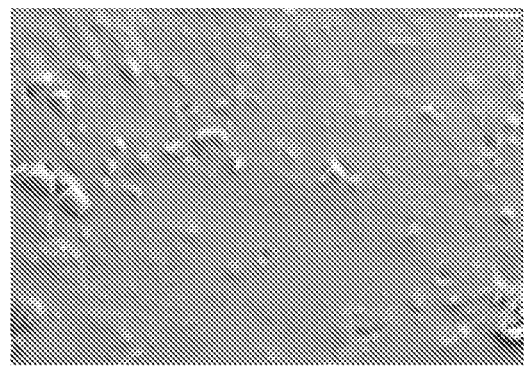
FIG. 7 shows SEM images of freeze-dried pellets after the completion of the FD protocol shown in FIG. 6.
Figure 7:
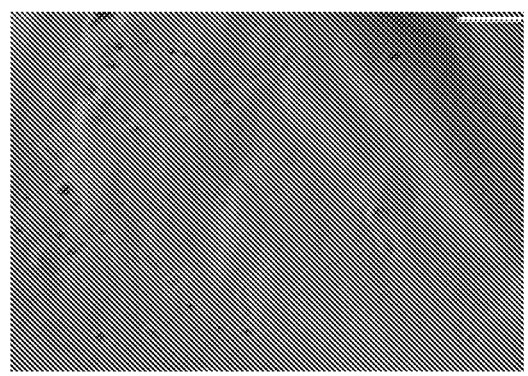
Figure 7:
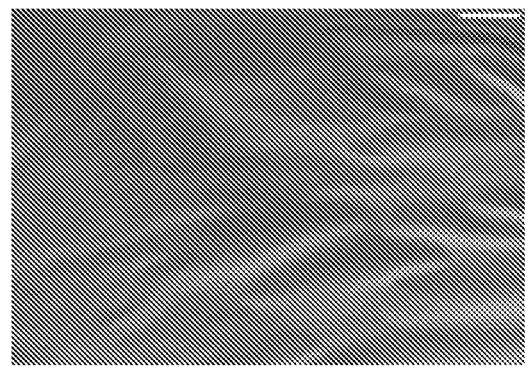

In contrast with the initial FD cycle, the pellets with NPs obtained with this cycle have higher $a_w$ and residual water content than the control sample. FIG. 7 shows SEM images of freeze-dried pellets after the completion of the FD protocol shown in FIG. 6. Scale bar is 2 μm. FIG. 7 shows that the microstructure is similar in all the cases regardless of the presence of nanoparticles. Furthermore, the microstructure is comparable to the one obtained with the initial FD protocol, shown in FIG. 2.

Figure 8A:
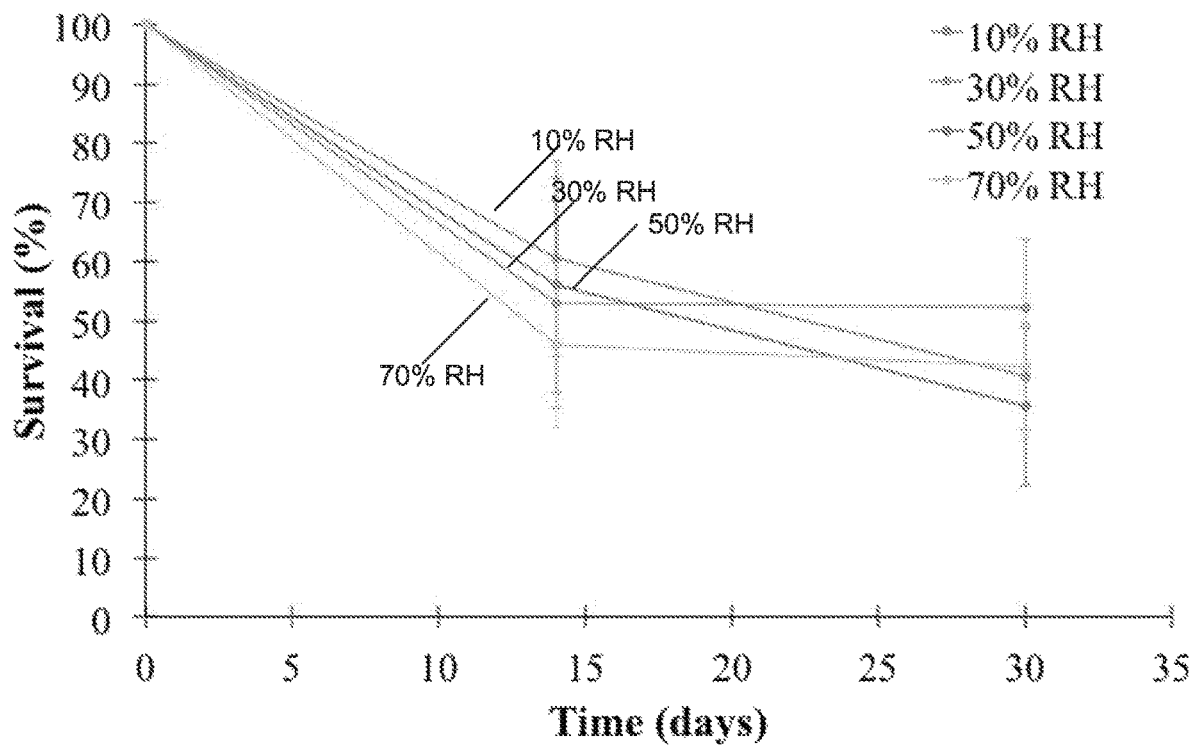
FIGS. 8(a) and 8(b) shows the accelerated decay test results for a control sample that underwent the conservative FD protocol in FIG. 6.
Figure 8B:
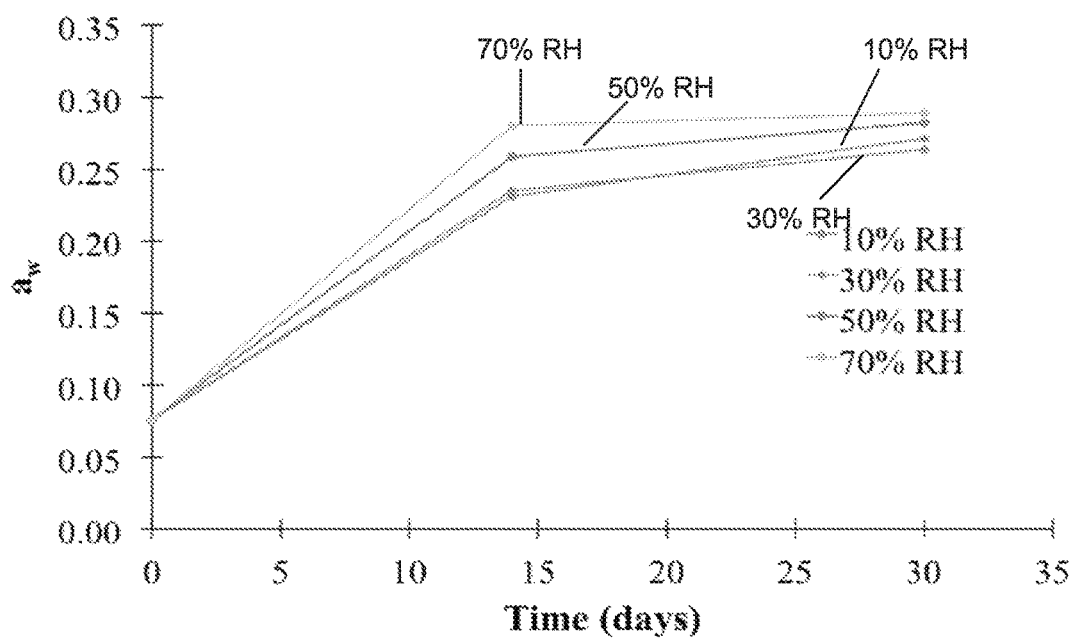

FIGS. 8(a) and 8(b) shows the accelerated decay test results for a control sample that underwent the conservative FD protocol in FIG. 6. Compared to FIG. 3(a), the survival rates are greatly improved with the conservative FD cycle. After 30 days in the incubator, the average survival rate is around 50%. Despite an initial low value of $a_w$, control pellets uptake a larger amount of water compared to the initial FD cycle as shown by comparing FIG. 8(b) to FIG. 3(b). During the first 14 days, the increase in $a_w$ is on average 0.20 units, which represents double the amount of water uptake exhibited in the initial FD cycle. Nonetheless, $a_w$ remains fairly constant after the initial increase, as well as a relatively constant value of survival rate. A correlation between the relative humidity of the chamber and the survival rate or between the relative humidity and $a_w$ was not observed.

Figure 9A:
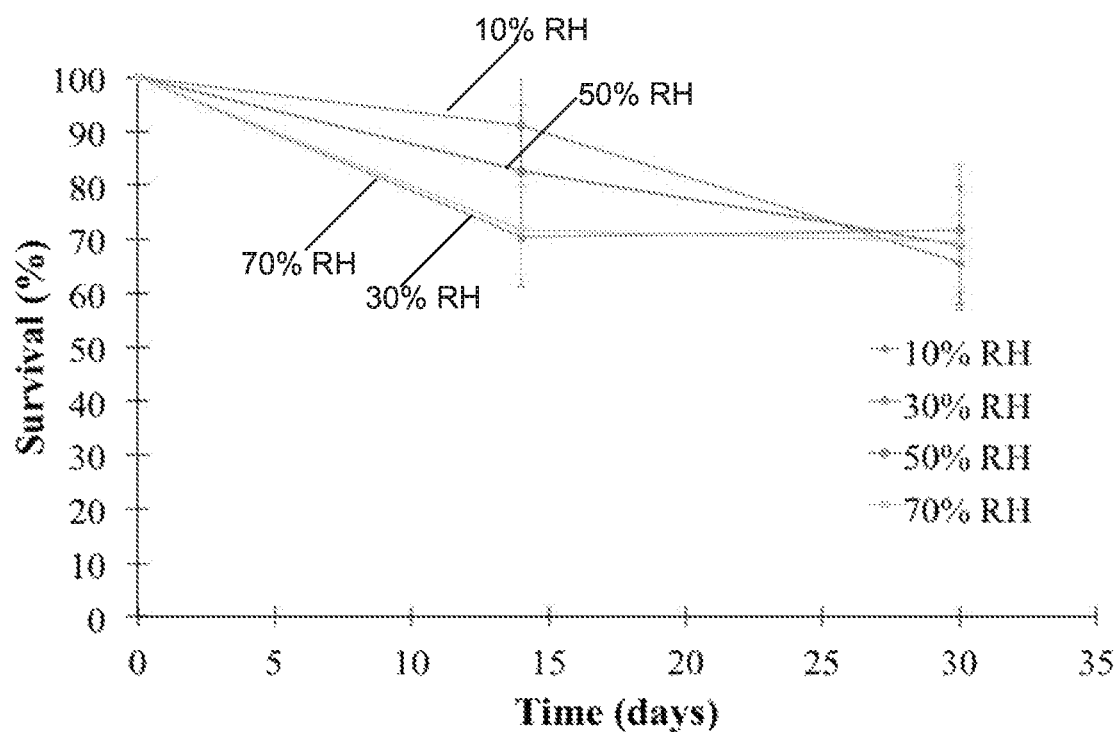
FIGS. 9(a) and 9(b) shows the accelerated decay test results for a 2 wt % CaP NP sample that underwent the conservative FD protocol in FIG. 6.
Figure 9B:
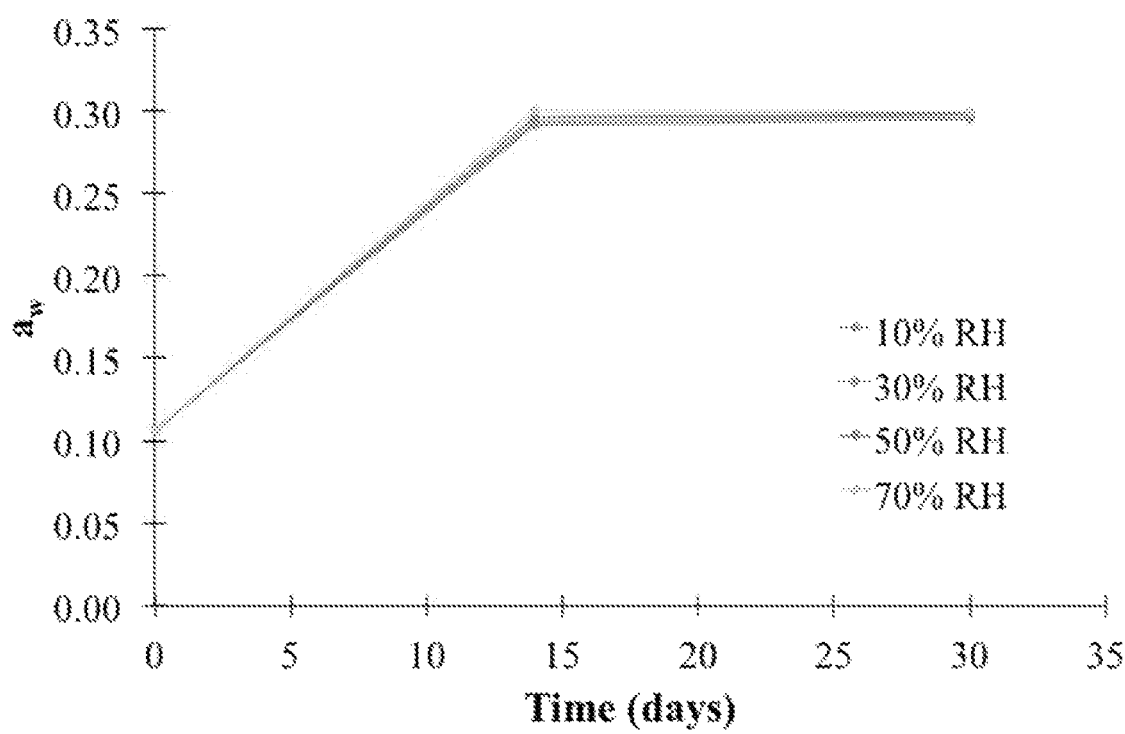

FIGS. 9(a) and 9(b) shows the accelerated decay test results for a 2 wt % CaP NP sample that underwent the conservative FD protocol in FIG. 6. FIG. 9(a) shows that the bacterial survival profile is improved compared to FIG. 4(a). After 30 days in the incubator, the survival was around 70%. This represents an improvement of 40% compared to control samples. The initial $a_w$ is higher than in the control, but the water uptake during the first two weeks of the test was similar, with an increase in 0.20 units. The improved stability compared to control may be due to the NPs helping to trap water at any time of the test. This explains the higher initial water content as well as high values of $a_w$ during the decay test.

Figure 10A:
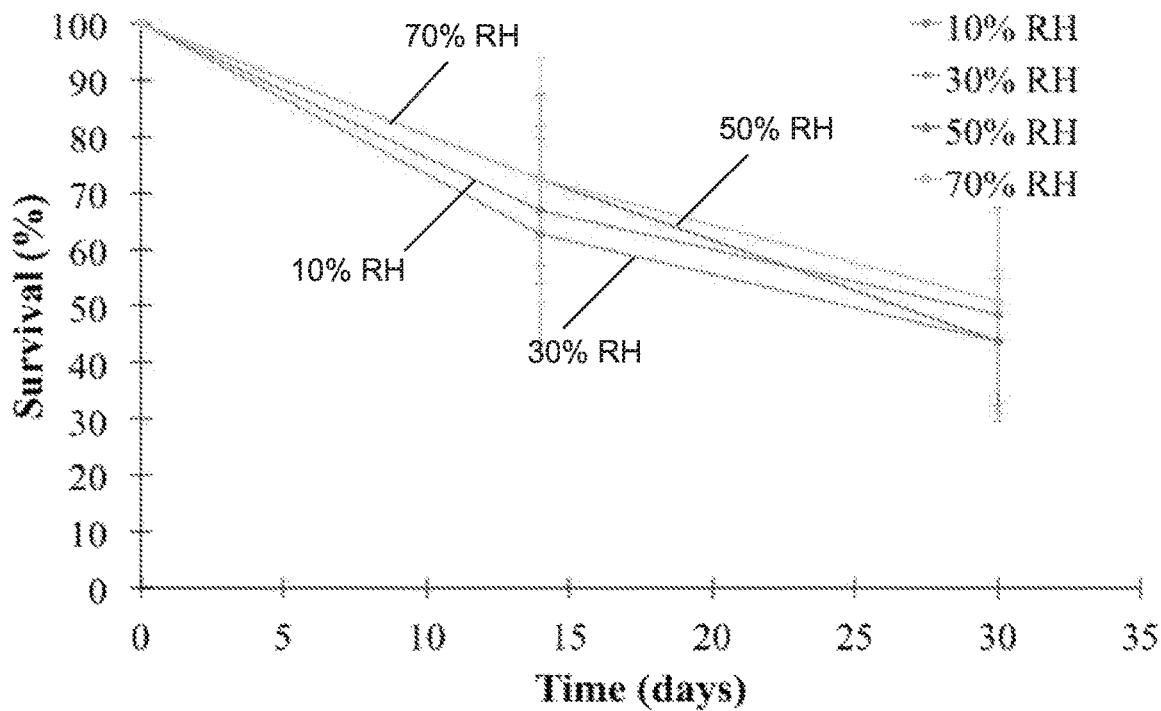
FIGS. 10(a) and 10(b) shows the accelerated decay test results for a 3 wt % CaP NP sample that underwent the conservative FD protocol in FIG. 6.
Figure 10B:
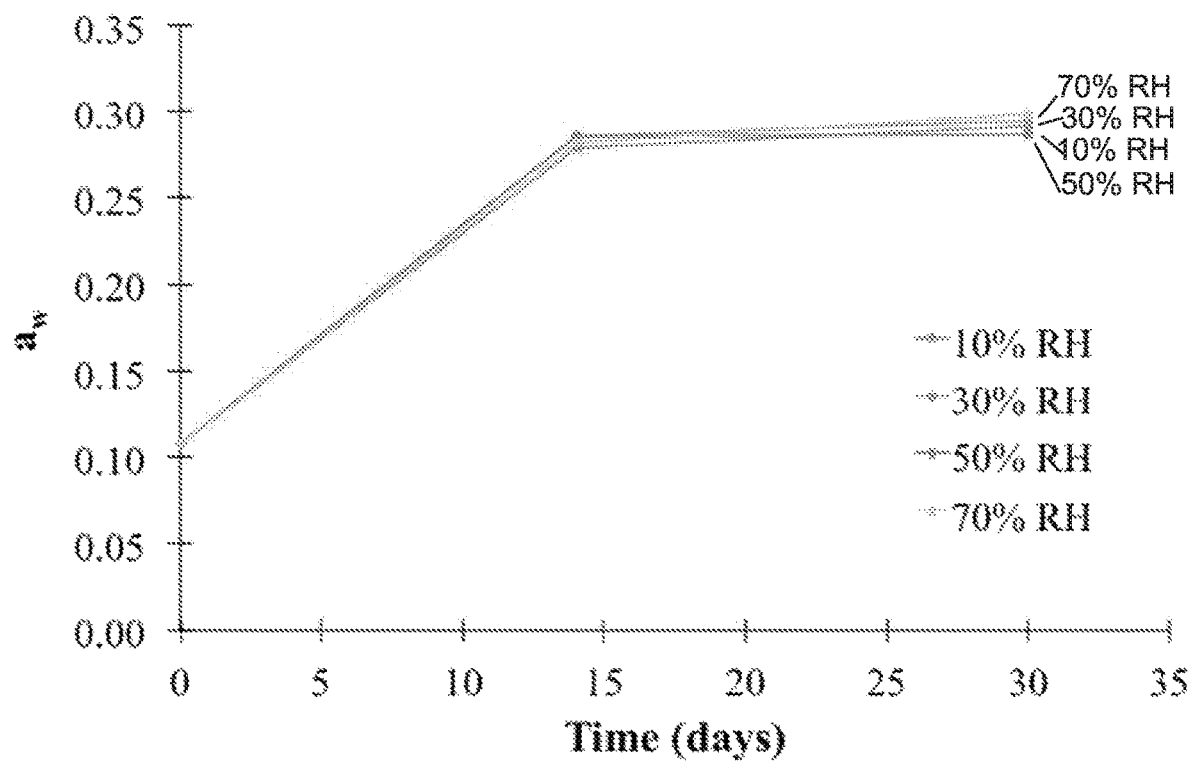

FIGS. 10(a) and 10(b) shows the accelerated decay test results for a 3 wt % CaP NP sample that underwent the conservative FD protocol in FIG. 6. The survival after 30 days is around 50%, comparable to the control pellets. The uptake in $a_w$ is similar to the 2 wt % CaP NPs pellets. This result suggests that more NPs do not necessarily translate into more efficient water sinks and that an optimal concentration of NPs give the highest survival rate for CaP NPs.

Figure 11A:
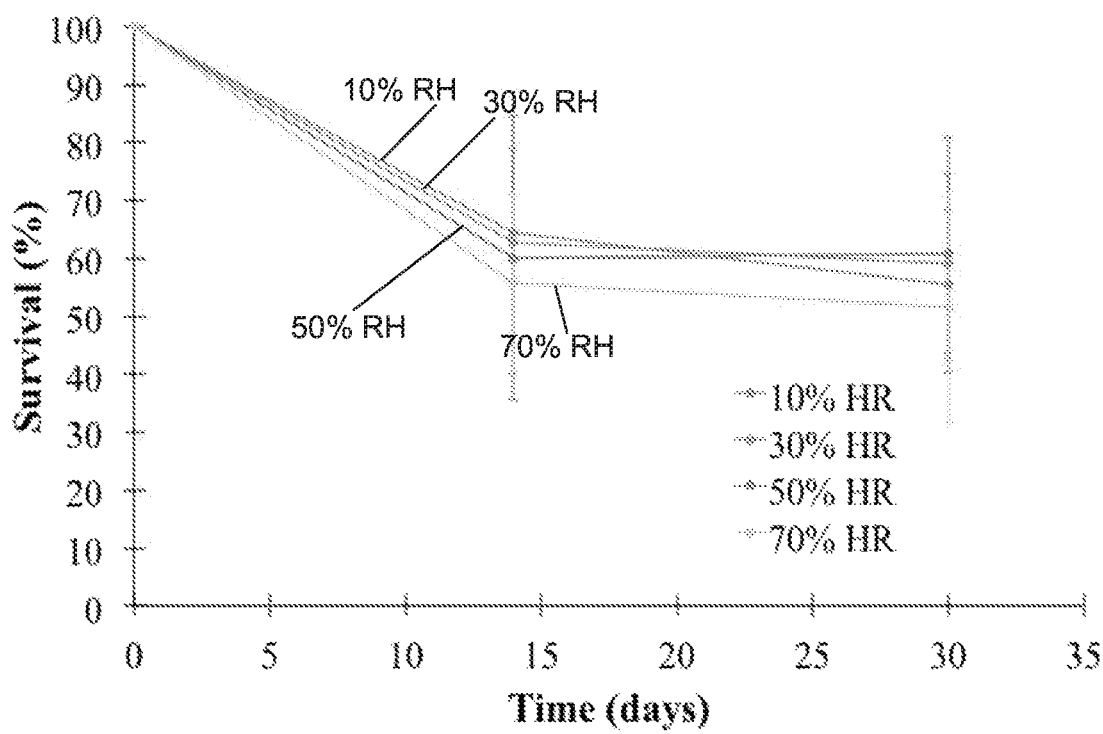
FIGS. 11(a) and 11(b) shows the accelerated decay test results for a 2 wt % starch NP sample that underwent the conservative FD protocol in FIG. 6.
Figure 11B:
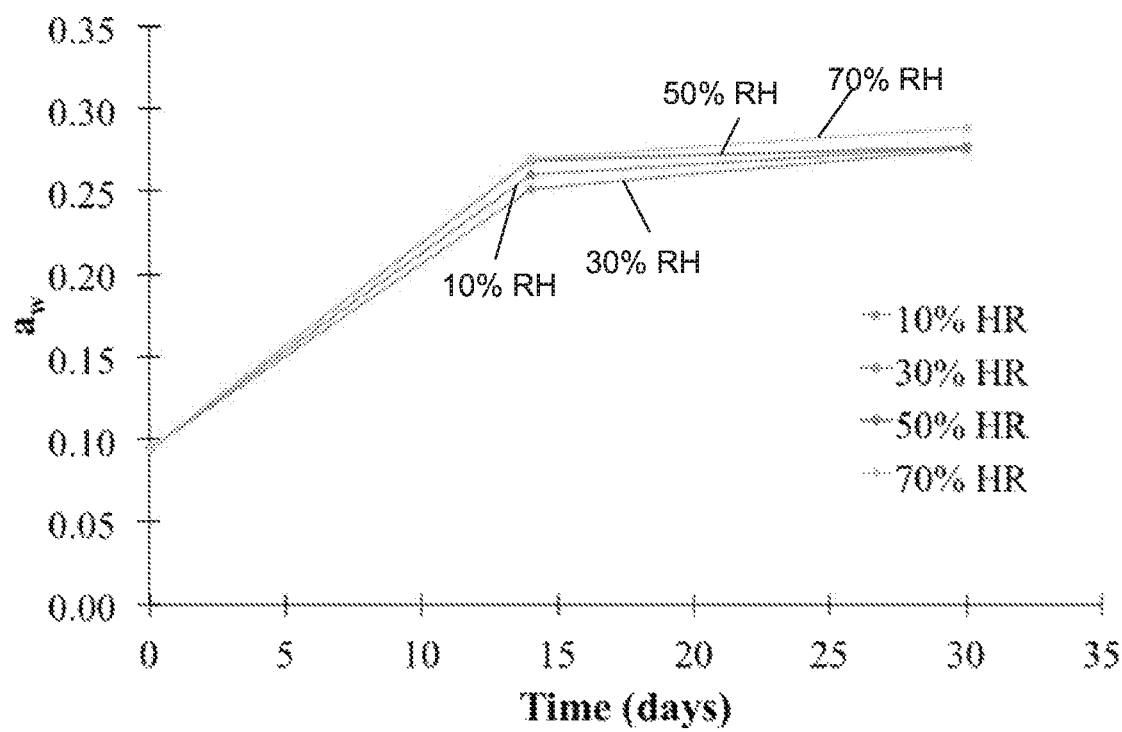

FIGS. 11(a) and 11(b) shows the accelerated decay test results for a 2 wt % starch NP sample that underwent the conservative FD protocol in FIG. 6. The survival rate after 30 days is on average 60%, which represents an improvement of 20% compared to control pellets. In this case the increase of $a_w$ is only 0.15 units, which is lower than in CaP NPs pellets and control pellets. The decay profile is improved compared to FIG. 5(b), given the lower initial $a_w$ obtained with the initial FD protocol.

The size, shape, and concentration of the nanoparticles may vary. For example, a largest dimension may range from 50 nm to 1 micron (average). The nanoparticles may be nanospheres or other shapes. In some embodiments, the nanoparticles may constitute between 1% and 5% by weight of the aqueous solution prepared prior to freeze-drying. Concentrations outside of this range may be used in other embodiments.

As indicated above, in certain embodiments, the nanoparticles are polymer-stabilized CaP nanoparticles. Such nanoparticles are described in PCT Publication No. 2017/209823, incorporated by reference herein. As described therein, the CaP nanoparticles include calcium ions and phosphate ions with an ionic polymer, thereby forming stable hybrid nanoparticles. According to various embodiments, the polymer-stabilized CaP nanoparticles may be polycation-stabilized (CaP/polymer$^{(+)}$ nanoparticles) or polyanion-stabilized (CaP/polymer$^{(-)}$ nanoparticles).

The CaP/polymer nanoparticles can be freeze-dried and stored for months with no loss of properties or changes to their morphology. The polymer-stabilized CaP nanoparticles may be referred to alternately as hybrid CaP/polymer nanoparticles or hybrid polymer/CaP nanoparticles. In some embodiments, the nanoparticles include amorphous CaP particles. The size of amorphous CaP/polymer hybrid nanoparticles can be finely tuned in a range from 10 nm to 1 μm by controlling the polymer identity and composition, concentration, molecular weight, initial salt concentration, and mixing order. To form the nanoparticles, in some embodiments, a phosphate ion solution at physiological conditions is combined with a polycation solution to form a suspension of phosphate/polymer aggregates. Subsequently, a calcium ion solution can be added to the phosphate/polymer complexes to yield CaP/polymer(+) nanoparticles. Examples of cationic polymers include poly(allylamine hydrochloride), poly(allylamine), poly(ethyleneimine), poly(vinylpyridine) salts, poly(L-lysine), chitosan, gelatin, poly(diallyldimethylammonium chloride), and protamine.

In another example, polyanion may be added to calcium to make a calcium/polymer complex, followed by addition of a phosphate solution to yield CaP/polymer(−) nanoparticles. Examples of anionic polymers include poly(aspartic acid), poly(acrylic acid), poly(acrylic acid sodium salt), poly(methacrylic acid) salts, poly(styrenesulfonic acid) salts, poly(2-acrylamido-2-methylpropane sulfonic acid), DNA, carboxymethyl cellulose, amelogenin, osteopontin, sulfonated dextran, poly(glutamic acid), poly(vinylphosphonic acid), poly(vinyl sulphonic acid), and carboxymethyl chitosan.

Example 1: Bacterial Formulations

*Lactobacillus acidophilus* LYO 50 DCU-S (DuPont Danisco) was purchased as a lyophilized powder from Dairy Connection, Inc. (Madison, WI). The powder was reconstituted in MRS broth (BD, Sparks, MD). After reconstitution the solution was preserved with an equimolar solution of trehalose and potassium phosphates (Sigma Aldrich, Milwaukee, WI), and mixed for at least 30 minutes. After this time the nanoparticles were added (if present) and the solution was mixed for 30 minutes. Following the mixing step, the solution was dripped over liquid nitrogen to allow the formation of spherical pellets. The pellets were later transferred to a −80° C. freezer.

Example 2: Preparation of PAH/CaP Hybrid Nanoparticles

Stock solutions of Poly(allylamine hydrochloride) (PAH, MW=200000 g/mol, Alfa-Aeser) (30 mg/mL), calcium chloride dihydrate ($CaCl_2 \cdot 2H_2O$) (1 M) and potassium phosphate dibasic ($K_2HPO_4$) (0.5 M) were prepared in Tris-buffered saline (TBS 1×) and the pH was adjusted to 7.4. The positively charged hybrid nanoparticles were prepared by first mixing the PAH stock solution (v=15 mL) with 135 mL phosphate stock solution diluted to c=15 mM concentration by TBS. Immediately after, 150 mL calcium stock solution diluted to 30 mM was added to the PAH/phosphate complex mixture without stirring. The suspensions were then centrifuged at 13000 rpm for 20 min, washed with ethanol, stored at −80° C. and freeze-dried at −4° C. for 24 h. A control sample was also prepared using the same concentrations described above but in the absence of polymers.

Example 3: Preparation of Starch Nanoparticles

Starch nanoparticles were prepared by an alkali freezing treatment method. Briefly, 10 grams of dry corn starch were dispersed into a sodium hydroxide-urea aqueous solution (0.6:0.4:99, NaOH:Urea:$H_2O$), stirred for 10 min, stored in at −80° C. for 24 hours, and then thawed by ultrasonication treatment (Branson 450 analog sonifier, Emerson Electric) at 80% power output for 20 min at 8±1° C., to obtain a homogeneous and viscous dispersion. Finally, the viscous dispersion was dialyzed against distilled water.

Example 4: Freeze Drying

Two FD protocols were loaded into a VirTis Advantage Plus freeze-dryer (SP Scientific, Stone Ridge, NY). The samples were stored in a −80° C. freezer. Prior to the beginning of the cycle, the shelf temperature was set to −40° C., and aluminum trays were placed on top of the shelf After allowing sufficient time to equilibrate, the frozen pellets were placed on top of the aluminum trays. During primary drying, the shelf temperature was set between −20 and 30° C. with a chamber pressure of 100 mTorr. During secondary drying, the shelf temperature was set at 30° C.

Example 5: Characterization of Intermediate Products and Freeze-Dried Products Differential Scanning Calorimetry: The measurements were obtained with a DSC-Q100 (TA Instruments, New Castle, DE). The samples were sealed in aluminum hermetic pans and then cooled down to −20° C., allowed to equilibrate for at least 5 minutes, heated up to 100° C. and equilibrated, cooled down to −10° C. and equilibrated, and heated up to 100° C. All the heating and cooling rates were 10° C./min and dry nitrogen was purged at 50 mL/min. To determine the glass transition temperature ($T_g$), the last scan was selected and analyzed using Universal Analysis software (TA Instruments, New Castle, DE). A point before and after the transition was manually selected, and the software calculated the tangent lines before and after the transition, as well as the midpoint. As customary, $T_g$ was reported as the midpoint.

For samples in a liquid state, aluminum hermetic pans were used. Before each pan was sealed, around 20 μL of sample was placed inside the pan. Following the closing of the pan, it was submerged in liquid nitrogen and allowed to equilibrate. The DSC was cooled to −90° C. and the pan was transferred to the measuring cell. After the transfer, the pan was allowed to equilibrate for at least 10 minutes inside the cell at −90° C. Then the sample was heated to 100° C. at a rate of 10° C./min, while gaseous nitrogen was purged at 50 mL/min. To determine the glass transition temperature of the freeze-concentrate ($T_g'$), the heating scan was selected and analyzed using the same methodology as with solid samples.

Karl Fisher titration and water activity: To estimate the water content of the samples at different points of the process and times of decay, a Karl Fisher coulometric equipment (Metrohm 737 KF, Switzerland) was used. Hydranal Coulomat AG (Sigma Aldrich, Milwaukee, WI) was selected as the Karl Fisher reagent. To complement these results, water activity ($a_w$) was also measured using a Rotronic Hygrolab C1 equipment (Hauppage, NY).

Long-term stability: The FD bacterial samples were prepared using the FD protocols described above. After FD, a sample was taken to be evaluated using the pour-plate technique. This sample was recorded as zero days. The rest of the pellets were placed in sealed Mylar bags and loaded into an incubator at 38° C. for up to a month. After this time, the samples were taken out of the incubator and evaluated. The stability was calculated as the amount of CFU/g measured at the time of measurement divided by the initial amount of bacteria. MRS broth (BD, Sparks, MD) was used to reconstitute the bacteria and plated with MRS agar (BD). An anaerobic environment was achieved using $CO_2$ sachets (BD).

Scanning Electron Microscopy: The freeze-dried pellets were removed from the freeze-dryer and transported to a desiccator jar at 10% relative humidity. The pellets were cut into two halves and fixed to the SEM stage using a copper conductive tape. The cut pellets were coated with a 8 nm layer of palladium/platinum using a sputter coater Ted Pella Cressington 208 HR (Redding, CA). All samples were sputtered at 40 mA and a pressure of 0.03 mbar. The coated pellets were imaged using a Field Emission-Scanning Electron Microscope (FE-SEM) Carl Zeiss Merlin (Germany).

The invention claimed is:

1. A composition comprising:
   a biological material, wherein the biological material is a microorganism;
   a polyhydroxyl compound; and
   polymer-stabilized calcium phosphate nanoparticles,
   wherein the composition is freeze-dried;
   wherein a water activity $a_w$ of the freeze-dried composition is less than 0.2,
   and wherein the polymer-stabilized calcium phosphate nanoparticles comprise amorphous polymer-stabilized calcium phosphate nanoparticles.

2. A composition comprising:
   a biological material, wherein the biological material is a microorganism;
   polyhydroxyl compound; and
   polymer-stabilized calcium phosphate nanoparticles,
   wherein the composition is an aqueous solution; and wherein the polymer-stabilized calcium phosphate nanoparticles constitute between 1-5% by weight of the aqueous solution.

3. The composition of claim 1, wherein the polyhydroxyl compound is a monosaccharide, a disaccharide, or a polysaccharide.

4. The composition of claim 1, wherein the polyhydroxyl compound is trehalose.

5. The composition of claim 1, wherein the biological material is a lactic acid bacteria.

6. The composition of claim 1, wherein the biological material is a probiotic.

7. The composition of claim 1, wherein water in the composition is concentrated in the polymer-stabilized calcium phosphate nanoparticles.

8. A method comprising:
   mixing a microorganism, a polyhydroxyl compound, and polymer-stabilized calcium phosphate nanoparticles in an aqueous solution;
   drying the aqueous solution to form a solid;
   performing a freeze-drying (FD) protocol to sublimate ice crystals in the solid and form the composition of claim 1.

9. The method of claim 8, wherein the polyhydroxyl compound is a monosaccharide, a disaccharide, or a polysaccharide.

10. The method of claim 8, wherein the polyhydroxyl compound is trehalose.

11. The method of claim 8 wherein the microorganism is a lactic acid bacteria.

12. The composition of claim 1, wherein the polymer-stabilized calcium phosphate nanoparticles are distributed throughout the composition.

13. A composition comprising:
    a biological material;
    a polyhydroxyl compound; and
    starch nanoparticles,
       wherein the composition is freeze-dried;
       wherein the biological material comprises a microorganism or a yeast;
       and wherein the starch nanoparticles constitute between 1% and 5% of an aqueous solution of the biological material, polyhydroxyl compound and starch nanoparticles prior to freeze-drying.

14. The composition of claim 13, wherein the starch nanoparticles are distributed throughout the composition.

15. The composition of claim 1, wherein the polymer-stabilized calcium phosphate nanoparticles comprise polycation-stabilized calcium phosphate nanoparticles or polyanion-stabilized calcium phosphate nanoparticles.

16. The composition of claim 15, wherein the polycation-stabilized calcium phosphate nanoparticles comprise poly(allylamine hydrochloride), poly(allylamine), poly(ethyleneimine), poly(vinylpyridine) salts, poly(L-lysine) or poly(diallyldimethylammonium chloride).

* * * * *